United States Patent [19]

Green

[11] 4,402,444

[45] Sep. 6, 1983

[54] SURGICAL STAPLING INSTRUMENT WITH AUTOMATIC FRAME REINFORCEMENT

[75] Inventor: David T. Green, Norwalk, Conn.

[73] Assignee: United States Surgical Corporation, Norwalk, Conn.

[21] Appl. No.: 255,887

[22] Filed: Apr. 20, 1981

[51] Int. Cl.³ ............................................. A61B 17/04
[52] U.S. Cl. ..................................... 227/19; 72/410; 128/334 R; 227/135; 227/DIG. 1
[58] Field of Search ................. 72/409, 410; 128/325, 128/326, 334 R; 227/19, DIG. 1, 83, 107, 129, 139, 135

[56] References Cited

U.S. PATENT DOCUMENTS

| | | | |
|---|---|---|---|
| 2,344,071 | 3/1944 | Wilson et al. | 227/DIG. 1 |
| 3,017,637 | 1/1962 | Sampson | 227/DIG. 1 |
| 3,080,564 | 3/1963 | Strekopitov et al. | 227/DIG. 1 |
| 3,252,643 | 5/1966 | Strekopytov et al. | 277/109 |
| 3,269,630 | 8/1966 | Fleischer | 227/107 |
| 3,275,211 | 9/1966 | Hirsch et al. | 227/124 |
| 3,315,863 | 4/1967 | O'Dea | 227/19 |
| 3,494,533 | 2/1970 | Green et al. | 227/19 |
| 3,589,589 | 6/1971 | Akopov | 227/153 |
| 3,692,224 | 9/1972 | Astafiev et al. | 227/19 |
| 3,795,034 | 3/1974 | Strekopytov et al. | 29/212 D |
| 3,935,981 | 2/1976 | Akopov et al. | 227/19 |
| 4,111,206 | 9/1978 | Vishnevsky et al. | 128/305 |
| 4,216,891 | 8/1980 | Behlke | 227/30 |

FOREIGN PATENT DOCUMENTS 406832 12/1924 Fed. Rep. of Germany .
906791 9/1962 United Kingdom .
1276239 6/1972 United Kingdom .

OTHER PUBLICATIONS

J. M. Kroyer et al., "Morphologic Liver Changes in Intestinal Bypass Patients", American Journal of Surgery, vol. 139, Jun. 1980, pp. 855–859.
W. O. Griffen, Jr., et al., "Symposium; Morbid Obesity", Contemporary Surgery, vol. 17, Jul. 1980, pp. 54–92.
K. Murphy et al., "Gastric Bypass for Obesity", American Journal of Surgery, vol. 140, Dec. 1980, pp. 747–750.
R. I. MacArthur, et al., "Revision of Gastric Bypass", American Journal of Surgery, vol. 140, Dec. 1980, pp. 751–754.

Primary Examiner—Paul A. Bell
Attorney, Agent, or Firm—Robert R. Jackson; John E. Nathan

[57] ABSTRACT

In a surgical stapling instrument in which tissue is stapled between the opposing legs of a U-shaped frame, the staple carrying assembly automatically engages the free ends of both legs of the frame to structurally reinforce the frame during operation of the instrument.

36 Claims, 10 Drawing Figures

SURGICAL STAPLING INSTRUMENT WITH AUTOMATIC FRAME REINFORCEMENT

BACKGROUND OF THE INVENTION

This invention relates to surgical stapling instruments, and more particularly to surgical stapling instruments in which the stapling is performed between two opposing legs of a substantially rigid frame.

Among the known surgical stapling instruments are those which include a substantially rigid frame having two opposing legs with a staple crimping anvil mounted on one leg and a staple carrying assembly and actuator mechanism mounted relatively to the other leg. One example of such an instrument is shown in Strekopitov et al. U.S. Pat. No. 3,080,564. Typically in such instruments, the two opposing legs are part of a U-shaped portion of the frame. In order to use the instrument, the staple carrying assembly is retracted and the U-shaped portion of the frame is placed around the tissue to be stapled. The staple carrying assembly is then advanced toward the anvil by operation of the actuator mechanism to clamp the tissue between the staple carrying assembly and the anvil. Thereafter, the actuator mechanism is further operated to cause the staples to be driven from the staple carrying assembly, through the tissue, and against the anvil, thereby crimping the staples and stapling the tissue. The instrument is removed from the stapled tissue by retracting the now-empty staple carrying assembly to release the clamping of the tissue.

During use of instruments of the type described above, considerable force is exerted on the frame of the instrument in a manner which tends to drive the opposing legs of the frame apart. All of the forces required to clamp the tissue and to drive and crimp the staples cumulate so that the maximum force tending to separate the legs of the frame can be very high. Depending on the size of the instrument, the number of staples, and the kind of tissue involved, this force may be several hundred pounds in known instruments and in known applications of those instruments.

The frame-distorting forces described above can have deleterious effects on the performance of the instrument. Particularly if the staple carrying assembly and anvil are mounted relative to respective opposite legs of the frame, distortion of the frame can cause misalignment of the anvil and the staple carrying assembly so that the staples do not enter the anvil pockets properly and therefore are not properly crimped. The anvil and the staple carrying assembly may also not remain parallel to one another so that some staples (especially those near the open end of the U-shaped portion of the frame) may not reach the anvil sufficiently for complete crimping.

In order to eliminate or ameliorate these problems, some instruments of this type have been provided with alignment and/or clamping means adjacent the normally open side of the U-shaped portion of the frame. In Green et al. U.S. Pat. No. 3,494,533, for example, a threaded pin is mounted adjacent the normally open side of the frame so that after the instrument is in position on the tissue, the pin can be extended across the open side of the frame and threaded into the opposite frame leg to clamp the frame legs together. This prevents the legs of the frame from spreading apart during subsequent tissue clamping and staple driving.

The use of frame reinforcement of the type described above produces good results, but it also adds several steps to the operation of the instrument and may increase the number of hands required to operate the instrument.

The problems associated with frame distortion are particularly aggravated in large instruments which are required to drive a large number of staples simultaneously. For example, there is increasing interest in using large instruments of this type for placing one or more rows of staples transversely across a major portion of the stomach in a procedure known as gastric bypass. One of the purposes for which this procedure is used is to reduce the effective size of the stomach and thereby reduce the intake of food by individuals who are extremely obese (a condition known as morbid obesity). The instruments sometimes used for performing this procedure simultaneously drive approximately 30 staples in an array of two parallel rows approximately 90 mm in length. Because of the considerable span of the instrument and the large forces involved, the problems associated with distortion of the frame of the instrument can be particularly severe in this procedure.

In some procedures there is interest in applying more staples than can be applied at one time by any of the presently available surgical stapling instruments. In the gastric bypass procedure mentioned above, for example, there have been occasional reports that a double row of staples may not be sufficient in some cases. The stress on the staple line may be so great that the staples tear away, thereby allowing the stomach to return to its original size. Additional staples would therefore be desirable to increase the strength of the staple line and reduce the risk of staples tearing out. Although additional staples can be applied by multiple use of the available instruments, it would be preferable to have an instrument which was capable of applying more staples in a single operation. Increasing the number of staples driven, however, further increases the forces which the instrument must be able to apply and withstand, and makes frame distortion an even more serious problem.

In view of the foregoing it is an object of this invention to improve and simplify surgical stapling instruments of the type in which tissue is stapled between the two opposing legs of the instrument frame.

It is a more particular object of this invention to provide surgical stapling instruments of the type mentioned above in which the frame is automatically reinforced in the vicinity of the two opposing legs during actuation of the instrument.

It is another more particular object of the invention to provide surgical stapling instruments of the type described above which are capable of simultaneously applying substantially more staples than is possible with the presently available instruments, while at the same time substantially reducing or preventing distortion of the frame in the vicinity of the two opposing legs.

SUMMARY OF THE INVENTION

These and other objects of the invention are accomplished in accordance with the principles of the invention by providing a surgical stapling instrument in which the staple carrying assembly includes means for releasably engaging the ends of both legs of the frame adjacent the normally open portion of the periphery of the frame in order to structurally tie those ends of the legs together and thereby reinforce the frame, and in which the staple carrying assembly is mounted so that, as the instrument is actuated, the means for releasably enaging the ends of the frame legs automatically moves into position to reinforce the frame before the staples are driven from the staple carrying assembly. Because the frame is securely and automatically reinforced before the staples are driven, the instrument can be designed to simultaneously drive substantially more staples than is typical in the presently available instruments.

Further features of the invention, its nature and various advantages will be more apparent from the accompanying drawing and the following detailed description of the invention.

DETAILED DESCRIPTION OF THE INVENTION

Although the invention is applicable to surgical stapling instruments having a variety of configurations, the invention will be fully understood by those skilled in the art from the following detailed description of an illustrative embodiment. For example, although the illustrative embodiment has a screw-type actuator mechanism similar to the actuator mechanism shown in FIGS. 18–22 of copending, commonly assigned U.S. patent application Ser. No. 188,691, filed Sept. 29, 1980, it will be understood that other types of actuator mechanisms such as the lever-type mechanism shown in FIGS. 1–10 of the same patent application could alternatively be used if desired. Similarly, although the illustrative embodiment is intended as a totally disposable instrument (i.e., an instrument which is sold loaded with staples and in a sterile condition, and is intended to be completely discarded after a single use, thereby avoiding all difficulty and expense associated with cleaning, sterilizing, and reloading the instrument for repeated use), it will be understood that the instrument could be made permanent and reusable if desired. For example, the major portion of the instrument could be made permanent and could be designed to accept disposable staple cartridges and/or disposable anvils in a manner generally similar to that shown in O'Dea U.S. Pat. No. 3,315,863.

As another example of possible variation in the instruments of this invention, the illustrative embodiment is particularly adapted for performing the gastric bypass procedure mentioned above. As such, the illustrative embodiment is a heavy-duty instrument capable of embracing an entire transverse section of the stomach and simultaneously driving a total of more than 50 staples in four parallel rows across a major portion of that transverse section, while leaving a minor portion of the transverse section unstapled to provide a small bypass lumen. Instruments constructed in accordance with this invention need not have all of these particular features. For example, the instrument could be designed to apply a different number of staples in a different array including a smaller or larger number of rows. Similarly, the instrument could be designed to apply staples through all the tissue embraced by the instrument without leaving any portion unstapled.

Figure 1:
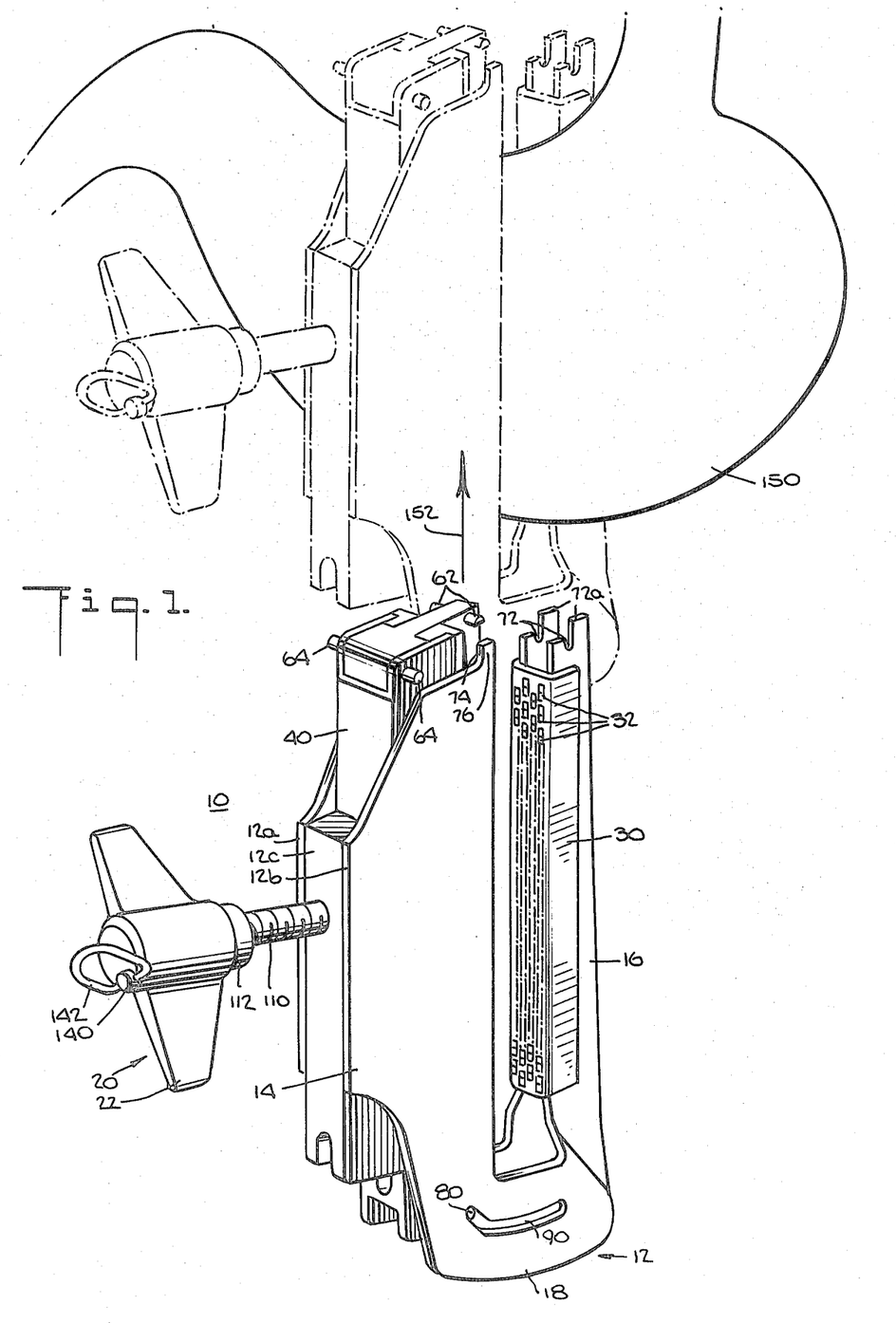
FIG. 1 is a perspective view in solid lines of an illustrative embodiment of the instrument of this invention, and shows in broken lines how the instrument can be applied to an illustrative tissue structure preparatory to stapling that tissue structure.

As shown in full lines in FIG. 1, illustrative instrument 10 includes U-shaped frame 12 defining two substantially parallel and opposing legs 14 and 16 which are rigidly joined together at one end by base portion 18. Frame 12 is made up of two spaced, substantially parallel metal plates 12a and 12b rigidly joined together along proximal leg 14 by spacer member 12c. Manually operable actuator assembly 20 is threadedly mounted on spacer member 12c. Staple crimping anvil 30 is fixedly mounted on distal leg 16 so that anvil pockets 32 face the interior of the U-shaped frame. Staple carrying assembly 40 is movably mounted in frame 12 between plates 12a and 12b so that staple guiding channels 46 (see, for example, FIG. 9) in the staple carrying assembly open out into the interior of the U-shaped frame.

Figure 7:
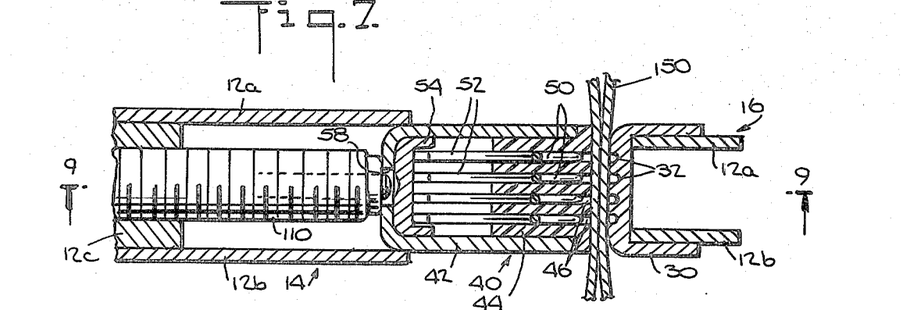
FIG. 7 is a partial cross sectional view taken along the line 7—7 in FIG. 6.
Figure 9:
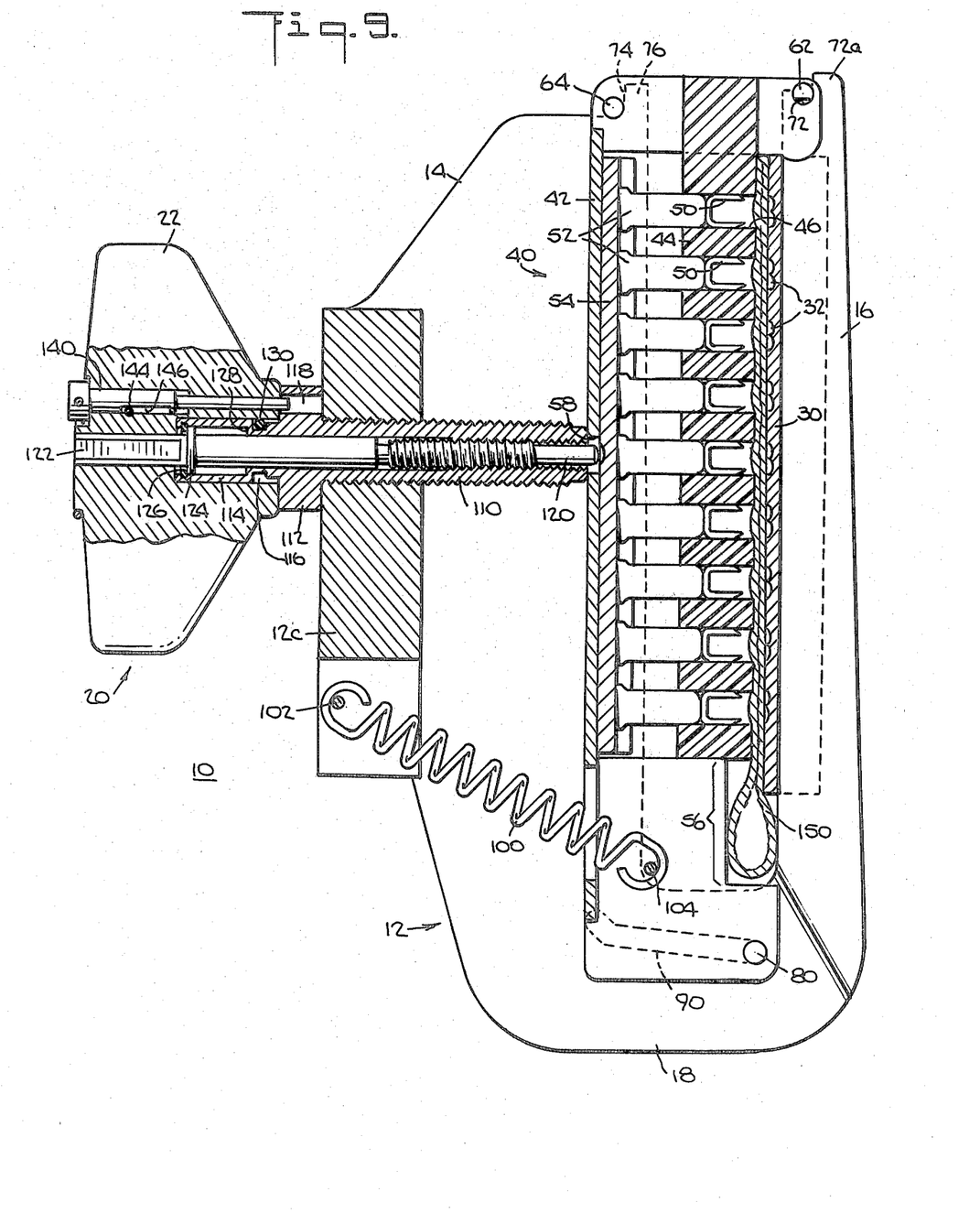
FIG. 9 is a cross sectional view taken along the line 9—9 in FIG. 7.

As may be best seen in FIGS. 7 and 9, staple carrying assembly 40 includes a rigid housing 42 which is guided by frame plates 12a and 12b. Housing 42 supports a staple guiding member 44 facing anvil 30 and having four parallel rows of parallel staple guiding channels 46. Each staple guiding channel initially contains one U-shaped metal staple 50 disposed in the associated staple guiding channel so that the legs of the staple point toward anvil 30. Behind each staple 50 in each staple guiding channel is a staple pusher 52. The proximal ends of all of staple pushers 52 are contacted by pusher actuator member 54, which initially rests against the inner surface of the proximal end of housing 42.

Figure 10:
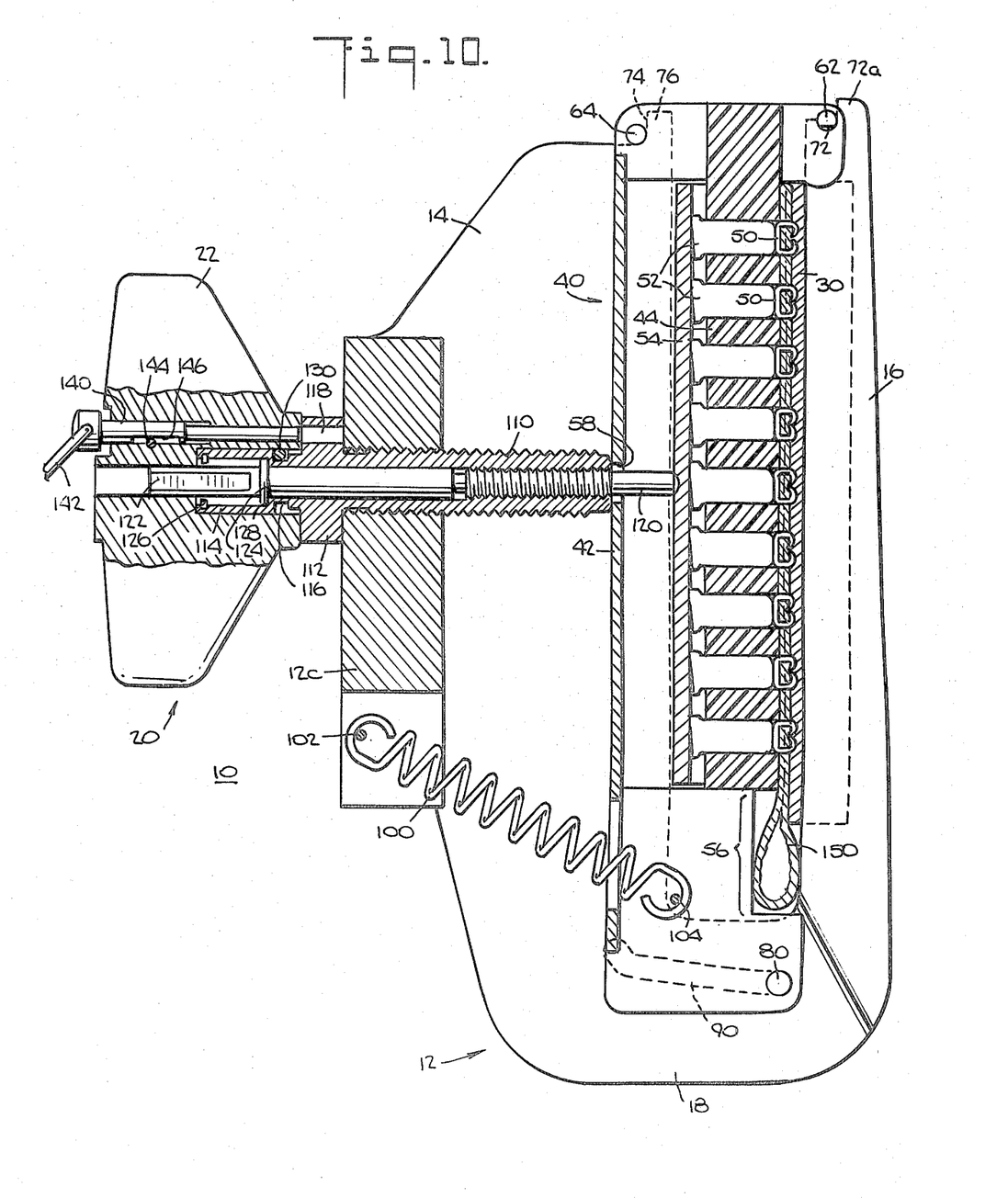
FIG. 10 is a cross sectional view taken along the line 10—10 in FIG. 8.

As best seen in FIGS. 9 and 10, the portion of staple guiding member 44 having staple guiding channels 46 extends along only a portion of the length of staple carrying assembly 40 parallel to proximal leg 14. Thus a portion 56 of the interior of the U-shaped frame does not have staples associated with it and tissue located in that portion of the instrument will not be stapled.

Returning to FIG. 1, the portion of staple carrying assembly 40 adjacent the open end of U-shaped frame 12 includes means for releasably engaging the adjacent ends of both of frame legs 14 and 16 during operation of the instrument to provide structural reinforcement of the frame across its normally open side or end. In the particular embodiment shown in the drawing, this portion of the apparatus includes a first pair of oppositely extending lugs 62 on the distal portion of the end of staple carrying assembly 40 adjacent the open end of the frame, and a second pair of oppositely extending lugs 64 on the proximal portion of the same end of the staple carrying assembly. Digital lugs 62 are adapted to fit in open-ended slots 72 in the free end of distal frame leg 16 (see, for example, FIG. 9). Proximal lugs 64 are adapted to engage the proximal surfaces 74 of projections 76, which extend from the free end of proximal frame leg 14, when lugs 62 are in slots 72. Additional details of these elements are discussed below in connection with the mounting of staple carrying assembly 40 and the operation of the instrument.

As shown for example in FIG. 1, staple carrying assembly 40 is mounted in frame 12 by means of two identical, coaxial lugs 80 (only one of which is visible in the drawing) extending from opposite sides of the staple carrying assembly adjacent the base 18 of the U-shaped frame. Each of lugs 80 extends into a respective one of two identical cam slots 90 in the adjacent portions of frame plates 12a and 12b. Lugs 80 and the proximal ends of cam slots 90 cooperate to form a first pivotal mounting for staple carrying assembly 40. It will be observed that the pivotal axis of this first pivotal mounting (i.e., the common axis of lugs 80) is adjacent the closed end of the U-shaped frame and substantially perpendicular to the plane defined by the U-shaped frame.

Staple carrying assembly 40 is resiliently biased in the proximal direction by tension coil spring 100 (see, for example, FIG. 9) extending between pin 102 in spacer member 12c and pin 104 in staple carrying assembly 40. Spring 100 tends to hold lugs 80 against the proximal ends of cam slots 90, and also tends to pivot staple carrying assembly 40 counter-clockwise about the first pivotal axis so that it rests against spacer member 12c when actuator assembly 20 is fully retracted as shown, for example, in FIGS. 1 and 2. In this position staple carrying assembly 40 is completely retracted from the region between frame legs 14 and 16 so that the instrument can be freely positioned around tissue to be stapled (or freely removed from tissue which has been stapled).

Actuator assembly 20, described in greater detail below, has two coaxial actuator shafts 110 and 120. As seen for example in FIGS. 9 and 10, outer actuator shaft 110 is threadedly engaged through spacer member 12c and has a distal end which bears on the proximal surface of a central portion of staple carrying assembly housing 42. Distal advance of outer actuator shaft 110 advances staple carrying assembly 40 toward anvil 30 through a sequence of motions described in detail below until staple carrying assembly 40 is substantially parallel to anvil 30 with the tissue to be stapled firmly clamped between those two elements (see FIGS. 6, 7, and 9). With staple carrying assembly 40 in this position, the distal end of inner actuator shaft 120 is aligned with aperture 58 in staple carrying assembly housing 42. Further distal advance of outer actuator shaft 110 is then stopped, and continued operation of the actuator assembly causes inner actuator shaft 120 to advance distally relative to outer actuator shaft 110. This causes the distal end of inner actuator shaft 120 to contact the proximal surface of pusher actuator member 54 and to advance that member distally, thereby driving staples 50 out of staple guiding channels 46, through the tissue clamped in the instrument, and against anvil 30 (see FIGS. 8 and 10).

Figure 2:
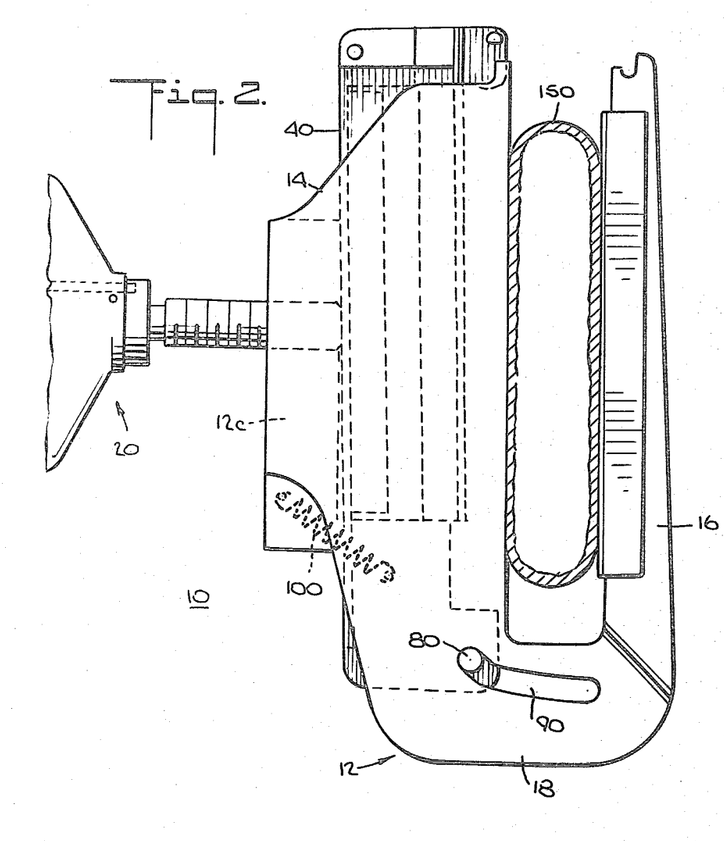
FIG. 2 is a partial side view of the instrument of FIG. 1 in position on the illustrative tissue structure of FIG. 1.

The motion of staple carrying assembly 40 in response to operation of actuator assembly 20 will now be considered. This motion sequence is illustrated by FIGS. 2-6. The initial position of actuator assembly 20 is as shown in FIGS. 1 and 2. In that position actuator assembly 20 is further retracted so that tension coil spring 100 holds lugs 80 against the proximal ends of cam slots 90 and pivots staple carrying assembly 40 counter-clockwise about the first pivotal axis defined by lugs 80 and the proximal ends of cam slots 90. Staple carrying assembly 40 therefore contacts spacer member 12c and is held completely out of the region between frame legs 14 and 16. The region between the frame legs is accordingly clear and the instrument can be positioned around the tissue 150 to be stapled, with one of frame legs 14 and 16 on each side of the tissue. For example, in FIG. 1 the tissue 150 is the stomach, and the instrument is positioned transversely across the stomach by moving the instrument from the full line position to the broken line position as indicated by the arrow 152.

Figure 3:
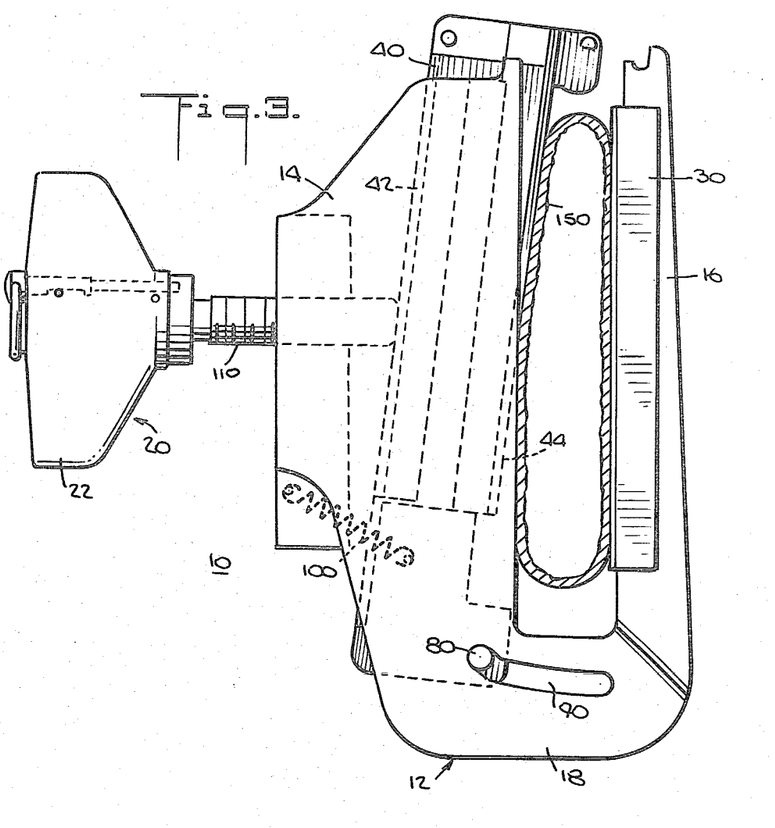
FIGS. 3–6 are views similar to FIG. 2 showing successive stages in the operation of the instrument.
Figure 4:
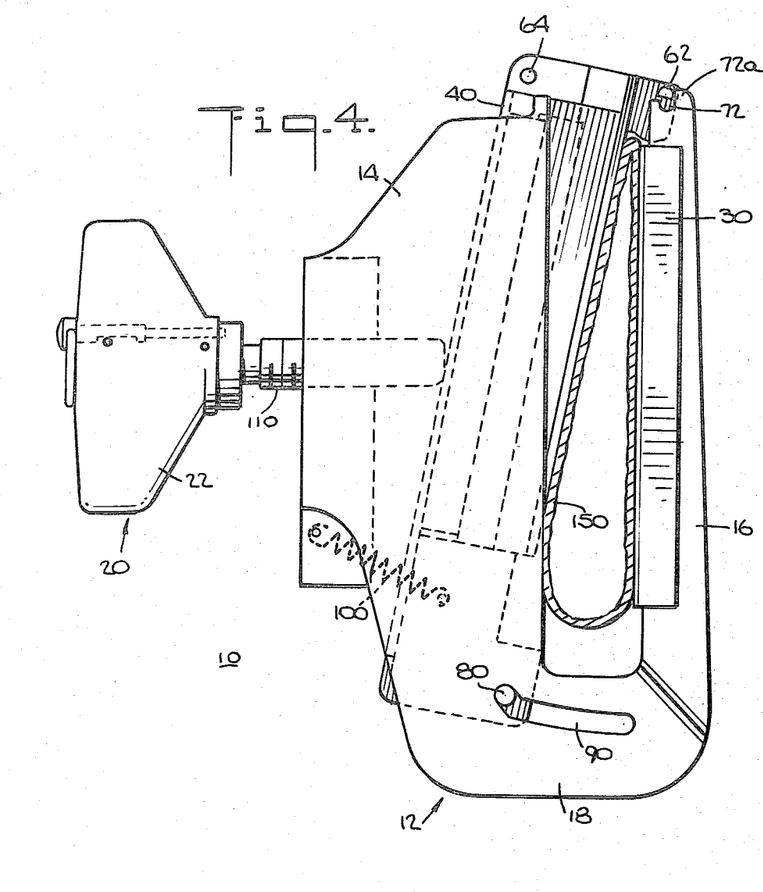

With the instrument in position around the tissue to be stapled, the handle 22 of actuator assembly 20 is rotated to rotate and thereby distally advance outer actuator shaft 110. This causes the distal end of outer actuator shaft 110 to contact staple assembly housing 42. Tension coil spring 100 still continues to hold lugs 80 against the proximal ends of cam slots 90. Accordingly, staple carrying assembly 40 begins to pivot clockwise as shown in FIGS. 3 and 4 about the first pivotal axis defined by lugs 80 and the proximal ends of cam slots 90. This causes the end portion of staple carrying assembly 40 adjacent the open end of frame 12 to begin to move toward the adjacent end of distal frame leg 16 and to begin to close that end of the frame. The adjacent portion of tissue 150 begins to be compressed between the face of staple guiding member 44 and anvil 30. It is an advantage of this invention that the open side of frame 12 is closed as shown in FIG. 4 by a portion of staple carrying assembly 40 before overall clamping of the tissue occurs. This is desirable because it prevents any tissue from being inadvertently extruded from the frame during tissue clamping.

Clockwise pivoting of staple carrying assembly 40 about the first pivotal axis defined by lugs 80 and the proximal ends of cam slots 90 continues in response to distal motion of outer actuator shaft 110 until, as shown in FIG. 4, lugs 62 contact stops 72a which project from the free end of distal frame leg 16 on the distal side of slots 72. Lugs 62 are flattened on the side toward tissue 150 to somewhat increase the clearance between the lugs and the portions of frame leg 16 defining the proximal sides of slots 72. This helps assure that lugs 62 will pass over those portions of frame leg 16 and contact stops 72a. The open end of frame 12 is now closed by the adjacent end portion of staple carrying assembly 40, and further clockwise pivoting of assembly 40 about the first pivotal axis defined by lugs 80 in contact with the proximal ends of cam slots 90 is prevented. However, tension coil spring 100 cooperates with outer actuator shaft 110 to continue to apply a clockwise torque to staple carrying assembly 40 which is sufficient to keep lugs 62 in contact with stops 72a until lugs 62 are pulled down into slots 72 as will now be described.

Figure 5:
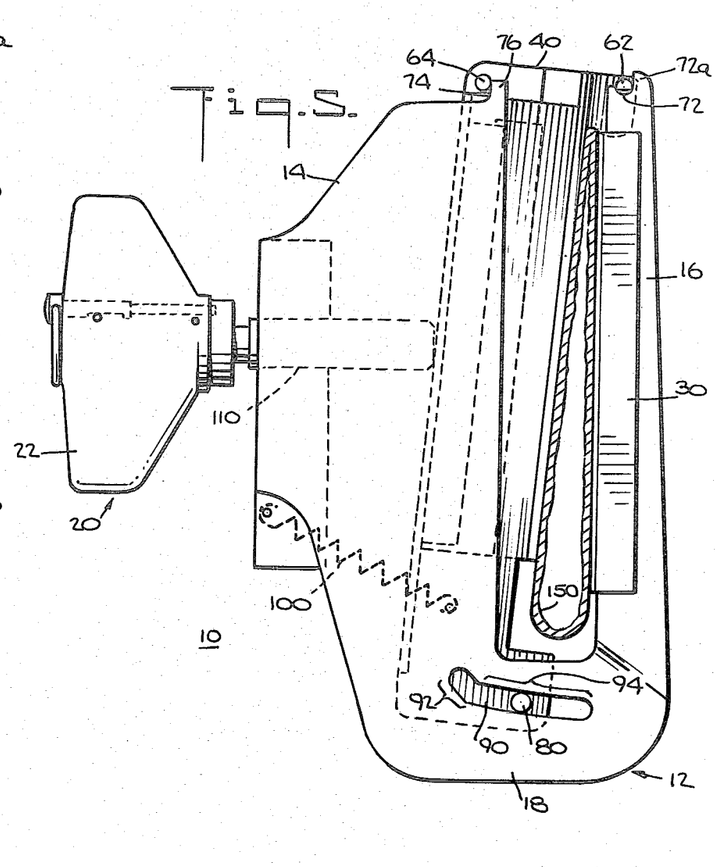

With clockwise pivoting of staple carrying assembly 40 stopped by contact of lugs 62 with stops 72a, further distal motion of outer actuator shaft 110 forces lugs 80 to move distally away from the proximal ends of cam slots 90. As shown, for example, in FIG. 5, the proximal portions 92 of cam slots 90 diverge from slots 72 in the distal direction. Accordingly, as lugs 80 follow proximal cam slot portions 92, the cam slots and lugs 80 cooperate to shift staple carrying assembly relative to frame 12 in the direction of frame base 18. This causes lugs 62 to be pulled down firmly into slots 72 as shown in FIG. 5. The remaining distal portions 94 of cam slots 90 are approximately uniformly distant from slots 72, so that lugs 62 are held in slots 72 as lugs 80 traverse distal cam slot portions 94.

As lugs 80 traverse portions 92 and 94 of cam slots 90 in the manner described above, it will be seen that staple carrying assembly 40 pivots counter-clockwise about a second pivotal axis defined by the common axis of lugs 62. Lugs 64 and proximal surfaces 74 of projections 76 on proximal frame leg 14 are positioned relative to one another so that very soon after lugs 62 have been pulled down into slots 72, and before lugs 80 have traversed the major portion of distal cam slot portions 94, lugs 64 begin to contact surfaces 74 as shown in FIG. 5. As soon as this contact between lugs 64 and surfaces 74 has been made, the previously free ends of frame legs 14 and 16 are tied together by the adjacent end portion of staple carrying assembly 40. This end portion of staple carrying assembly 40 therefore acts as a tension member to structurally reinforce frame 12.

As lugs 80 continue to traverse the distal portions 94 of cam slots 90, and as staple carrying assembly 40 continues to pivot counter-clockwise about the second pivotal axis defined by the common axis of lugs 62, lugs 64 travel a short distance down along surfaces 74. Surfaces 74 may diverge slightly from slots 72 in the direction of motion of lugs 64 in order to gradually tighten the reinforcing action of staple carrying assembly 40 on frame 12 as staple carrying assembly 40 approaches its final position parallel to anvil 30 and the forces acting on the frame accordingly increase.

Figure 6:
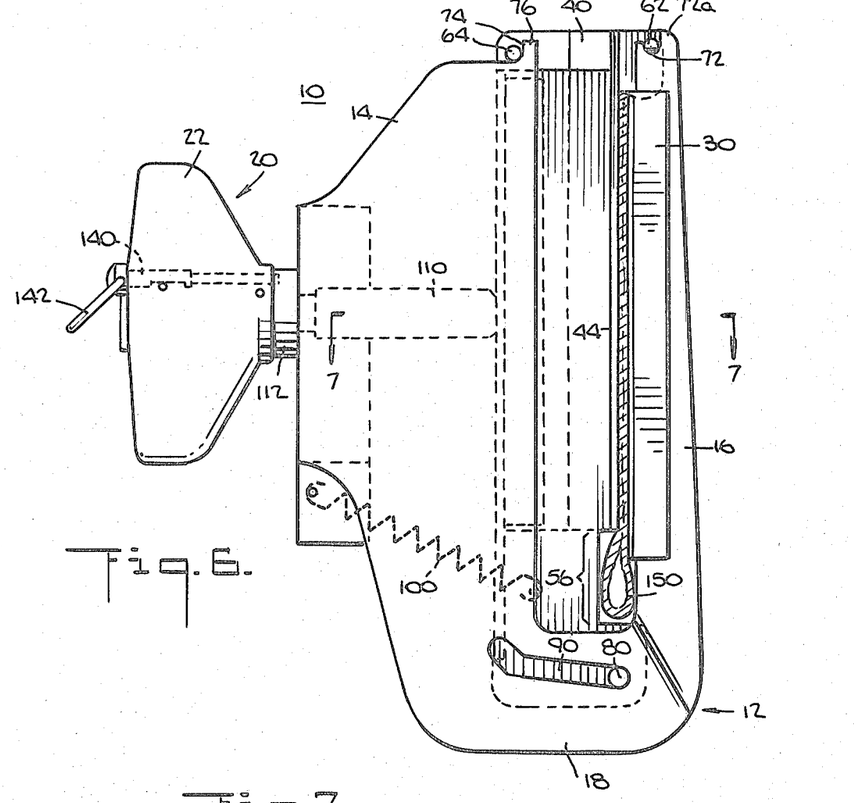

The counter-clockwise pivoting of staple carrying assembly 40 about the second pivotal axis defined by the common axis of lugs 62 gradually brings staple carrying assembly 40 into parallel alignment with anvil 30 as shown in FIGS. 6 and 9. As this occurs, the tissue to be stapled is gradually clamped between the opposing faces of staple guiding member 44 and anvil 30. The portion of tissue 150 which is to be left unstapled (i.e., the portion of tissue in region 56) is not clamped. The reinforcement of the originally open end of frame 12 by the adjacent portion of staple carrying assembly 40 substantially reduces or eliminates distortion of frame 12 as a result of the forces required to clamp the tissue to be stapled.

When staple carrying assembly 40 is parallel to anvil 30, lugs 80 contact the extreme distal ends of cam slots 90 as shown in FIGS. 6 and 9, thereby preventing any further counter-clockwise pivoting of the staple carrying assembly. This also prevents any further distal motion of outer actuator shaft 110. Further distal motion of outer actuator shaft 110 may also be simultaneously stopped by contact of annular collar 112 on shaft 110 with the proximal surface of spacer member 12c as best seen in FIG. 9. Staple clinching pockets 32 in anvil 30 and staple guiding channels 46 in staple carrying assembly 40 are relatively located so that when staple carrying assembly 40 is parallel to anvil 30 with the tissue to be stapled clamped therebetween, staple clinching pockets are located directly opposite each staple guiding channel 46 for clinching the staple to be driven from that channel. The instrument is thus ready for further operation to drive the staples.

Considering actuator assembly 20 now in somewhat more detail, as best seen in FIGS. 9 and 10, handle 22 is rotatably mounted on the proximal end portion 114 of outer actuator shaft 110. Handle 22 is retained on outer actuator shaft 110 by pin 130 which extends transversely through handle 22 and annular slot 116 in shaft 110. During the first portion of the operation of the instrument to clamp tissue in the instrument for stapling, outer actuator shaft 110 is made to rotate with handle 22 by pin 140 extending longitudinally through handle 22 into aperture 118 in outer actuator shaft collar 112 as shown in FIG. 9.

Inner actuator shaft 120 is threadedly mounted inside outer actuator shaft 110. Handle 22 is mounted relative to inner actuator shaft 120 so that it cannot rotate relative to that shaft, but so that shaft 120 can move longitudinally relative to handle 22. Relative rotation of elements 22 and 120 is prevented by flat surface 122 on the side of the proximal end portion of shaft 120 in cooperation with a corresponding flat surface (not shown) on the adjacent inner surface of the aperture in handle 22 which accepts the proximal end portion of shaft 120. Inner actuator shaft 120 is initially substantially retracted within outer actuator shaft 110 as shown in FIG. 9 so that collar 124 on shaft 120 is against retaining ring 126 on the inside of the proximal end portion of shaft 110.

Because shaft 110 is initially rotationally fixed relative to handle 22, and because shaft 120 is always rotationally fixed relative to handle 22, both of shafts 110 and 120 rotate with handle 22 during the first portion of the operation of the instrument to clamp the tissue. When lugs 80 reach the distal ends of cam slots 90 and the tissue to be stapled is fully clamped in the instrument, the distal end of inner actuator shaft 120 is aligned with aperture 58 in the proximal side of staple carrying assembly housing 42 as shown in FIG. 9. At that point, outer actuator shaft 110 cannot be advanced any farther and rotation of handle 22 stops. This indicates to the operator of the instrument that the tissue is fully clamped in the instrument and ready to be stapled. The operator then rotationally uncouples shaft 110 from handle 22 by retracting pin 140 from aperture 118 using finger ring 142 as shown in FIG. 10. Pin 140 is retained in handle 22 by any suitable means such as pin 144 extending transversely through handle 22 and longitudinal slot 146 in pin 140.

Figure 8:
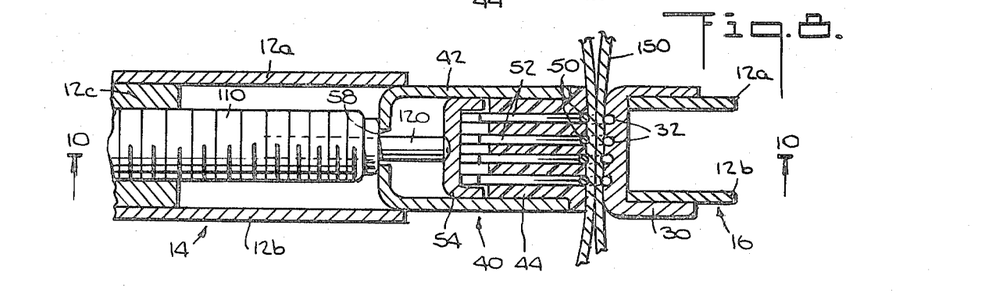
FIG. 8 is a view similar to FIG. 7 but showing a subsequent stage in the operation of the instrument.

With pin 140 withdrawn from aperture 118, rotation of handle 22 can be resumed. Now outer actuator shaft 110 is stationary relative to frame 12 and the distal end of that shaft maintains staple carrying assembly 40 in its tissue clamping position. Inner actuator shaft 120, on the other hand, continues to rotate with handle 22 and therefore advances distally relative to shaft 110 because of the threaded connection between the two shafts. Accordingly, the distal end of shaft 120 extends into staple carrying assembly 40 as shown in FIGS. 8 and 10, thereby advancing pusher actuator 54 and staple pushers 52 to drive staples 50. As staples 50 are driven, the parallel legs of the staples pass through the clamped tissue and are crimped by contact with pockets 32 in anvil 30, thereby securely stapling the tissue.

When inner actuator shaft 120 has advanced far enough to assure complete formation of the staples, further advance of shaft 120 is stopped by contact of inner actuator shaft collar 124 with annular surface 128 on the inside of outer actuator shaft 110. This again prevents further rotation of handle 22 and indicates to the operator that stapling is complete and that the instrument can be removed.

The instrument is removed from the stapled tissue by rotating handle 22 in the opposite direction from that required to clamp the tissue and drive the staples. The first portion of such opposite rotation of handle 22 retracts inner actuator shaft 120 within outer actuator shaft 110. When inner actuator shaft collar 124 contacts retaining ring 126, further opposite rotation of handle 22 retracts outer actuator shaft 110. This allows staple carrying assembly 40 to execute a motion sequence which is the reverse of the tissue clamping motion sequence. This reverse motion of staple carrying assembly 40 is powered by tension coil spring 100. The stapled tissue is thereby unclamped and the instrument is restored to the initial condition shown in FIGS. 1 and 2 so that the instrument can be removed from the stapled tissue.

While the invention is more broadly applicable as discussed above, the illustrative embodiment has several features which make that embodiment particularly suitable for use in the above-mentioned gastric bypass procedure. This procedure is illustrated in the several drawing Figures. The instrument is placed transversely across the stomach as shown in FIGS. 1 and 2. The transverse section of the stomach is then secured in the instrument as shown in the sequence of FIGS. 2–6 so that the major portion of the transverse section is clamped between staple guiding member 44 and anvil 30, while the remaining minor portion of the transverse section in region 56 is unclamped. Four parallel rows of staples 50 are then applied to staple together the opposite walls of the clamped portion of the stomach, while the unclamped portion in region 56 is left unstapled to provide a relatively small bypass lumen through which food can continue to pass. While the total number of staples applied may vary, in the preferred embodiment the total number of staples is typically more than 50, and most preferably more than 60. The instrument is then removed and the procedure is complete.

The four parallel rows of staples applied as described above provide a very strong staple pattern which is highly resistant to being broken as a result of the tissue tearing away from one or more staples. By the same token, the forces required to clamp so much tissue and drive so many staples simultaneously are very large and make the frame reinforcement feature of this invention particularly important. For example, the maximum force required to operate an instrument of the illustrated type may be 1000 pounds or more. Such forces would severely distort the frame of the instrument unless reinforced in accordance with this invention.

It will be understood that the foregoing is merely illustrative of the principles of the invention, and that various modifications can be made by those skilled in the art without departing from the scope and spirit of the invention. For example, for procedures other than the gastric bypass procedure, all of the tissue in the instrument may be clamped and stapled by extending anvil 30 and staple guiding member 44 along substantially the entire length of frame legs 14 and 16. Similarly, although four parallel rows of staples are driven in the illustrative embodiment, a greater or smaller number of rows may be employed, or the staples may be driven in any other suitable pattern.

I claim:

1. A surgical stapling instrument comprising:
   frame means having a normally open peripheral portion for admitting tissue to be stapled into an interior region of the frame means;
   staple driving means for stapling tissue located in the interior region of the frame means, the staple driving means being movably mounted relative to the frame means;
   actuator means for causing the staple driving means to move relative to the frame means to clamp the tissue located in the interior region of the frame means against a portion of the frame means in preparation for stapling the tissue; and
   means responsive to the motion of the staple driving means for automatically forming a structural connection between portions of the frame means adjacent both sides of the normally open peripheral portion to substantially prevent the portions of the frame means thus structurally connected from spreading apart during stapling of the tissue.

2. The apparatus defined in claim 1 wherein the staple driving means is mounted relative to the frame means adjacent one side of the interior region, and wherein the portion of the frame means against which the tissue is clamped is the opposite side of the interior region and includes staple clinching means.

3. The apparatus defined in claim 2 wherein the means for forming a structural connection comprises:
   a tension member mounted in the staple driving means; and
   means for mounting the staple driving means so that the motion of the staple driving means in response to the actuator means causes each of two spaced portions of the tension member to move adjacent and engage a respective one of the portions of the frame means to be structurally connected, the tension member thereafter providing the structural connection between those portions of the frame means.

4. The apparatus defined in claim 3 wherein the tension member is mounted on a portion of the staple driving means adjacent the normally open peripheral portion of the frame means, and wherein the staple driving means is mounted so that the staple driving means responds to the actuator means by first pivoting so that the two spaced portions of the tension member move adjacent the respective portions of the frame means to be structurally connected.

5. The apparatus defined in claim 4 wherein the staple driving means is further mounted so that when the two spaced portions of the tension member are adjacent the respective portions of the frame means to be structurally connected, the staple driving means further responds to the actuator means by causing the tension member to move laterally relative to its tension axis to cause at least one of the spaced portions of the tension member to engage the adjacent portion of the frame means.

6. The apparatus defined in claim 5 wherein the staple driving means is still further mounted so that after the lateral motion of the tension member, the staple driving means responds still further to the actuator means by pivoting in a direction opposite the direction of first pivoting.

7. The apparatus defined in claim 6 wherein an initial portion of the pivoting of the staple driving means in the opposite direction causes the second of the spaced portions of the tension member to engage the adjacent portion of the frame means.

8. The apparatus defined in claim 7 wherein a subsequent portion of the pivoting of the staple driving means in the opposite direction causes the staple driving member to clamp the tissue to be stapled against the staple clinching means.

9. The apparatus defined in claim 1 further comprising means responsive to release of the actuator means for automatically releasing the structural connection.

10. A surgical stapling instrument comprising:
    a U-shaped frame;
    anvil means mounted on a first leg of the frame;
    staple carrying means including means for releasably engaging both legs of the U-shaped frame adjacent the open end of the U to substantially prevent the legs of the frame from spreading apart when thus engaged;

means mounted on the second leg of the frame for actuating the staple carrying means; and means for mounting the staple carrying means relative to the frame so that in response to actuation of the staple carrying means by the means for actuating, the means for releasably engaging engages both legs of the U-shaped frame and the staple carrying means moves into parallel relationship with the anvil means.

11. The apparatus defined in claim 10 wherein the staple carrying means includes a rigid housing and wherein the means for mounting the staple carrying means comprises:

means for resiliently biasing a first end of the rigid housing adjacent the closed end of the U-shaped frame away from the adjacent portion of the anvil means; and first pivot means adjacent the first end of the rigid housing for allowing the staple carrying means to pivot about a first pivotal axis substantially perpendicular to the plane defined by the legs of the U.

12. The apparatus defined in claim 11 wherein the means for resiliently biasing tends to resiliently pivot the staple carrying means about the first pivotal axis in a direction away from the anvil means.

13. The apparatus defined in claim 11 wherein the means for actuating the staple carrying means comprises means for exerting an actuating force on the rigid housing at a first location intermediate the means for releasably engaging and the first pivot means, the actuating force being exerted along an axis substantially perpendicular to the first pivotal axis and the legs of the frame, and the actuating force being exerted in a direction tending to move the staple carrying means toward the anvil means.

14. The apparatus defined in claim 13 wherein the means for resiliently biasing comprises spring means for exerting a spring force on the rigid housing at a second location intermediate the first location and the first pivot means, the spring force having at least a component parallel to and opposite the actuating force.

15. The apparatus defined in claim 11 wherein the means for releasably engaging comprises first means for stopping the pivoting of the staple carrying means about the first pivotal axis toward the anvil means when the second end of the rigid housing adjacent the open end of the U-shaped frame is across the open end of the frame.

16. The apparatus defined in claim 15 wherein the first pivot means and the means for resiliently biasing allow the means for actuating to translate the second end of the rigid housing toward the adjacent portion of the anvil means only after the first means for stopping stops the pivoting of the staple carrying means about the first pivotal axis.

17. The apparatus defined in claim 16 wherein the means for releasably engaging further comprises second pivot means adjacent the second end of the rigid housing for cooperating with the adjacent end portion of the first leg of the frame when the first means for stopping stops the pivoting of the staple carrying means about the first pivotal axis for allowing the staple carrying means to pivot about a second pivotal axis substantially parallel to the first pivotal axis.

18. The apparatus defined in claim 17 wherein the means for mounting the staple carrying means further comprises means for causing the staple carrying means to move with a component of motion substantially parallel to the first leg of the frame during at least a portion of the pivotal motion of the staple carrying means about the second pivotal axis.

19. The apparatus defined in claim 18 wherein the means for causing the staple carrying means to move with a component of motion substantially parallel to the first leg of the frame comprises a cam and a cam follower, one of which is associated with each of the staple carrying means and the U-shaped frame.

20. The apparatus defined in claim 18 wherein the means for releasably engaging engages the first leg of the frame in response to the motion of the staple carrying means substantially parallel to the first leg of the frame.

21. The apparatus defined in claim 20 wherein the means for releasably engaging engages the second leg of the frame in response to the pivoting of the staple carrying means about the second pivotal axis.

22. The apparatus defined in claim 21 wherein the means for mounting the staple carrying means further comprises second means for stopping the pivoting of the staple carrying means about the second pivotal axis when the staple carrying means is substantially parallel to the anvil means.

23. The apparatus defined in claim 10 wherein, after the staple carrying means is in parallel relationship with the anvil means, the means for actuating drives a plurality of surgical staples from the staple carrying means, through tissue between the staple carrying means and the anvil means, and against the anvil means.

24. The apparatus defined in claim 23 wherein the staple carrying means carries staples adjacent only a portion of the length of the legs of the frame so that a portion of the tissue between the legs of the frame can remain unstapled after the staples have been driven.

25. The apparatus defined in claim 10 further comprising means responsive to release of the actuator means for causing the means for releasably engaging to release the legs of the U-shaped frame.

26. A surgical stapling instrument comprising:
a frame having a U-shaped portion for accepting tissue to be stapled between the legs of the U;
an anvil mounted on a first leg of the U;
a staple carrying assembly movably mounted relative to the second leg of the U, the staple carrying assembly being mounted by means of a cam and cam follower connection between a portion of the staple carrying assembly remote from the open end of the U and the adjacent portion of the frame, the cam and cam follower being pivotable relative to one another;
frame reinforcing means mounted on the portion of the staple carrying assembly adjacent the open end of the U;
spring means for resiliently biasing the staple carrying assembly away from the anvil and for resiliently pivoting the staple carrying assembly about the cam and cam follower connection so that the frame reinforcing means is resiliently biased away from the open end of the U; and
actuator means mounted relative to the second leg of the U for first pivoting the staple carrying assembly about the cam and cam follower connection so that the frame reinforcing means moves adjacent portions of both legs of the U adjacent the open end of the U, and thereafter causing the cam follower to traverse the cam so that the frame reinforcing means engages the adjacent portions of both legs of the U to prevent those portions of the frame from subsequently spreading apart during stapling of the tissue between the staple carrying assembly and the anvil.

27. The apparatus defined in claim 26 wherein the frame reinforcing means engages both legs of the U during a first portion of the traverse of the cam by the cam follower, and wherein the staple carrying assembly clamps the tissue to be stapled against the anvil during a subsequent portion of the traverse of the cam by the cam follower.

28. The apparatus defined in claim 27 wherein, after the tissue to be stapled has been clamped, the actuator means drives a plurality of staples from the staple carrying assembly, through the tissue, and against the anvil.

29. The apparatus defined in claim 28 wherein the staple carrying assembly contains four parallel rows of staples.

30. The apparatus defined in claim 29 wherein the staple carrying assembly contains at least 50 staples, all of which are driven simultaneously by the actuator means.

31. The apparatus defined in claim 28 wherein a portion of the staple carrying assembly between (a) the cam and cam follower connection and (b) the frame reinforcing means is at all times spaced from the adjacent portion of the first leg of the U so that the adjacent portion of the tissue accepted in the frame is not clamped or stapled to provide a bypass around the stapled portion of the tissue.

32. The apparatus defined in claim 26 further comprising means for allowing the actuator means to return to its initial condition, in response to which the spring means causes the cam follower to traverse the cam in the opposite direction and the frame reinforcing means releases the legs of the U.

33. The apparatus defined in claim 26 further comprising means for allowing the actuator to return to its initial condition, in response to which the spring means causes the cam follower to traverse the cam in the opposite direction and then causes the staple carrying assembly to pivot about the cam and cam follower connection so that the frame reinforcing means moves away from the open end of the U to allow the tissue to be removed from between the legs of the U.

34. A surgical fastening instrument comprising:
a U-shaped frame for accepting tissue to be fastened between the first and second legs of the frame;
anvil means mounted on the first leg of the frame;
fastener carrying means movably mounted relative to the second leg of the frame for clamping the tissue to be fastened against the anvil means and for driving at least one surgical fastener through the clamped tissue;
actuator means mounted on the frame for moving the fastener carrying means relative to the second leg of the frame so that the fastener carrying means clamps the tissue to be fastened against the anvil means; and
means for mounting the fastener carrying means relative to the frame so that the fastener carrying means responds to operation of the actuator means by first moving across and closing off the open side of the U-shaped frame and thereafter moving adjacent to the anvil means to clamp the tissue to be fastened against the anvil means.

35. The apparatus defined in claim 34 wherein the means for mounting the fastener carrying means comprises:
first means for causing the fastener carrying means to respond to operation of the actuator means by pivoting about a first pivotal axis adjacent the base of the U-shaped frame until the fastener carrying means has moved across and closed off the open side of the U-shaped frame; and
second means for causing the fastener carrying means to respond to operation of the actuator means by pivoting about a second pivotal axis adjacent the open side of the U-shaped frame after the fastener carrying means has moved across and closed off the open side of the U-shaped frame.

36. The apparatus defined in claim 34 wherein the fastener carrying means includes means for automatically engaging the first leg of the frame adjacent the open side of the U-shaped frame after the fastener carrying means has moved across and closed off the open side of the U-shaped frame but before the fastener carrying means has fully clamped the tissue to be fastened against the anvil means.

* * * * *

UNITED STATES PATENT AND TRADEMARK OFFICE
CERTIFICATE OF CORRECTION

PATENT NO. : 4,402,444
DATED : September 6, 1983
INVENTOR(S) : David T. Green

It is certified that error appears in the above—identified patent and that said Letters Patent is hereby corrected as shown below:

| Column | Line | |
|---|---|---|
| 1 | 14 | "relatively" should be --relative-- |
| 4 | 58 | "Digital" should be --Distal-- |
| 5 | 57 | "further" should be --fully-- |

Signed and Sealed this

Third Day of July 1984

[SEAL]

Attest:

GERALD J. MOSSINGHOFF

Attesting Officer

Commissioner of Patents and Trademarks